United States Patent
MacPhee et al.

(10) Patent No.: US 6,232,084 B1
(45) Date of Patent: May 15, 2001

(54) PLATELET FACTOR-4 RECEPTOR ASSAY (75) Inventors: Colin Houston MacPhee, Letchworth; Kitty Moores, Stevenage; Theodorus Antonius Berkhout, Hertford, all of (GB)

(73) Assignee: SmithKline Beecham plc (GB)

( * ) Notice: Subject to any disclaimer, the term of this patent is extended or adjusted under 35 U.S.C. 154(b) by 0 days.

(21) Appl. No.: 09/275,384

(22) Filed: Mar. 24, 1999

(30) Foreign Application Priority Data

Mar. 27, 1998 (GB) .................................................. 9806677

(51) Int. Cl.$^7$ .................................................. G01N 33/53

(52) U.S. Cl. .............................. 435/7.1; 436/501; 435/7.2

(58) Field of Search ..................... 435/7.1, 7.2; 436/501; 530/388.22

(56) References Cited

PUBLICATIONS

GenBank Accession No. U03905.
Loetscher M. et al., "TYMSTR, a putative chemokine receptor selectively expressed in activated T cells, Exhibits HIV–1 coreceptor function", Current Biology, vol.7(9) pp. 652–660 (1997).
Liao et al., "STRL33, A novel Chemokine Receptor–like Protein Functions as a fusion cofactor for both Macrophage–tropic and T–Cell Line tropic HIV–1", J. Exp. Med, vol. 185(11) pp. 2015–2023 (1997).
Deng et al., "Expression cloning of new receptors used by simian and human immunodeficiency viruses" Nature vol. 388, pp. 296–300 (1997).
Alkhatib et al., "A new SIV co–receptor, STRL33", Nature vol. 388, p. 238 (1997).
Farzan et al., "Two Orphan Seven–Transmembrane Segment Receptors which are expressed in CD4–Positive Cells Support Simian Immunodeficiency Virus Infection," J. Exp. Med., vol. 186(3), pp. 405–411 (1997).
Rucinski et al., Antiheparin Proteins Secreted by Human Platelets, Purification, Characterization and Radioimmunoassay Blood, vol. 53 (1)pp. 47–62 (1979).
Deuel et al., "Platelet factor 4 is chemotactic for neutrophils and monocytes", Proc. Acad. Natl. Sci., vol. 78(7) pp. 4584–87 (1981).
Senior et al., "Chemotactic Activity of Platelet Alpha Granule Proteins for Fibroblasts" J. Cell Biol., vol. 96, pp. 382–385 (1983).
Osterman et al., "The Carboxyl–Terminal Tridecapeptide of Platelet Factor 4 is a Potent Chemotactic Agent For Monocytes", Biochem. Biophys. Res Comm., vol. 107(1) pp. 130–135 (1982).

Goldman et al., "Inhibition of human neutrophil receptor–mediated uptake of N–formyl–met–leu–phe by Platelet factor 4 (59–70)", Immunology, vol. 54 pp. 163–172 (1985).

Barone et al., "The expression in *Escherichia coli* of Recombinant Human Platelet Factor 4, a Protein with Immunoregulatory Activity", J. Biol. Chem., vol. 263(18)pp. 8710–8715 (1988).

Yin et al., "Prevention by a Platelet–Derived Factor (Platelet Factor 4) of Induction of Low Dose Tolerance To Pneumococcal Polysaccharides", Cell. Immuno., vol. 115, pp. 221–227 (1988).

Maione et al., "Inhibition of Angiogenesis by Recombinant Human Platelet Factor–4 and related peptides", Science, vol. 247, pp. 77–79 (1990).

Van Damme et al., "Identification by sequence analysis of chemotactic factors for monocytes produced by Normal and transformed cells stimulated with virus, double–stranded RNA or cytokine", Eur J Immunol, vol. 19, pp. 2367–73 (1989).

Sharpe et al., "Induction of Local Inflammation by Recombinant Human Platelet Factor 4 in the Mouse", Cell. Immunol, vol. 137(1) pp. 72–80 (1991).

Engstad et al., "A Novel Biological effect of platelet factor 4(PF4): enhancement of LPS–induced tissue Activity in monocytes", J. Leukoc Biol., vol. 58(5) pp. 575–81 (1995).

Manco–Johnson, "Family issues in continuous infusion therapy with factor VIII", Blood Coag Fibrinolysis, vol. 7 Suppl (1), pp. S21–S25 (1996).

Osterud, "Cellular interactions in tissue factor expression by blood monocytes", Blood Coag Fibrinoly Fibrinolysis, vol. 6 Suppl (1) pp. S20–S25 (1995).

Charo et al., "Molecular cloning and functional expression of two monocyte chemoattractant protein 1 Receptors reveals alternative splicing of the carboxyl–terminal tails", Proc. Natl. Acad. Sci., vol. 91 pp. 2752–2756 (1994).

*Primary Examiner*—John Ulm
(74) *Attorney, Agent, or Firm*—William T. Han; Ratner & Prestia; William T. King

(57) ABSTRACT

The ligand PF-4 has been identifed as a ligand for the 7TM receptor HBMBU14, also known as TYMSTR, STRL-33 and BONZO.

12 Claims, 3 Drawing Sheets

Figure 1

Binding of $^{125}$I labelled PF-4 to RBL & CHO cells transfected with PF-4 receptor A. RBL: $IC_{50}$ = 2.7nM, Kd = 1.7

B. CHO: $IC_{50}$ = 11.1nM, Kd = 19.3

Figure 2

PF-4-stimulated chemotaxis in PF-4 receptor-transfected RBL and CHO cells

Figure 3

PF-4-stimulated chemotaxis in human monocytes

PLATELET FACTOR-4 RECEPTOR ASSAY

This invention relates to the identification of the ligand for an orphan 7TM receptor and its use as a screening tool to identify antagonists and agonists of the receptor, to the antagonists and agonists so identified and their use in therapy.

Chemokines are structurally and functionally related 8 to 10 kD polypeptides, involved in the recruitment of white blood cell into areas of inflammation and their subsequent activation (Miller, M. D. and Krangel, M. S. (1992) Crit. Rev. Immunol. 12, 17–46; Baggiolini, M., Dewald, B. and Moser, B.(1994) Adv. Immunol. 55, 97–179). In addition, some chemokines are able to regulate the proliferative potential of hematopoietic progenitor cells, endothelial cells and certain types of transformed cells (Oppenheimer, J. J., Zachariae, C. O. C., Mukaida, N., and Matsushima, K. (1991) Ann. Rev. Immunol. 9, 617–648; Schall, T. J. (1991) Cytokine 3, 165–183). Based on whether the first two cysteine moieties are separated by one amino acid residue or are adjacent, chemokines belong to the α- or CXC chemokine family (e.g interleukin (IL)-8) or the β- or CC chemokine family (e.g. RANTES and MCP-1). CXC chemokines play a key role in the accumulation of various cell types, including neutrophils, monocytes, T-lymphocytes, basophils and fibroblasts at sites of inflammation. These chemokines are implicated in both acute and chronic inflammatory disease states, including rheumatoid arthritis, inflammatory bowel disease, atherosclerosis, asthma, leprosy, psoriasis, various respiratory syndromes, and also contribute towards modulation of angiogenesis and fibroplasia.

Chemokines express their biological responses through interaction with chemokine receptors (Horuk, R. and Peiper, S. C. (1995) Exp. Opin. Ther. Patents 5, 1185–1200).

Several chemokine receptors have already been cloned, for instance, the following human CXC chemokine receptors:

the receptors for IL8 (CXCR1) and IL8/ELR chemokines, (CXCR2, Holmes, W. E., Lee, J., Kuang, W. J., Rice, G. C. and Wood, W. I. (1991) Science 253, 1278–1280; Murphy, P. M. and Tiffany, H. L. (1991) Science 253, 1280–1283);

a receptor for IP10/Mig (CXCR3, Loetscher, M., Gerber, B., Loetscher, P., Jones, S. A., Piali, L., Clark-Lewis, I., Baggiolini, M., and Moser, B. (1996) J. Exp. Med. 184, 963–969.);

a receptor for SDF-1 (CXCR4 or LESTR, Bleul, C. C., Farzan, M., Choe, H., Parolin, C., Clark-Lewis, I., Sodroski, J., Springer, T. A. (1996) Nature, 382, 829–836.)

In addition, the following human CC chemokine receptors:

MIP-1α/RANTES receptor (CCR-1, Neote, K., Digregorio, D., Mak, J. K., Horuk, R. and Schall, T. J. (1993) Cell 72, 415–425; Gao, B. J.-L., Kuhns, D. B., Tiffany, H. L., McDermott, D., Li, X., Francke, U. and Murphy, P. M. (1993) J. Exp. Med. 177, 1421–1427);

MCP-1A and B receptors (CCR-2A and B, Charo, I. F., Myers, S. J., Herman, A., Franci, C., Connolly, A. J. and Coughlin, S. R. (1994) Proc. Natl. Acad. Sci. USA 91, 2752–2756; Yamagami, S., Tokuda, Y., Ishii, K., Tanaka, T. and Endo, N. (1994) Biochem. Biophys. Res. Commun. 202, 1156–1162);

the eotaxin/RANTES receptor (CCR-3, Combadiere, C., Ahuja, S. K. and Murphy, P. M. (1995) J. Biol. Chem. 270, 16491–16494; Daugherry, D. L., Siciliano, S. J., DeMartino, J. A., Malkowitz, L., Sirotina, A. and Springer, M. S. (1996) J.Exp.Med. 183, 2349–2354; Kitaura, M., Nakajima, T., Imai, T., Harada, S., Combadiere, C., Tiffany, H. L., Murphy, P. M. and Yoshie, O. (1996) J. Biol Chem. 271, 7725–7730), the promiscuous receptor on basophils (CCR-4, Power, C. A., Meyer, A., Nemeth, K., Bacon, K. B., Hoogewerf, A. J., Proudfoot, A. E. I. and Wells, T. N. C. (1995) J. Biol. Chem. 270, 19495–19500);

a new MIP-1α/MIP-1β/RANTES receptor (CCR-5, Samson, M., Labbe, O., Mollereau, C., Vassart, G. and Parmentier, M. (1996) Biochemistry 35, 3362–3367.)

a new receptor for LARC (CCR6, Baba, M., Imai, T., Nishimura, M., Kakizaki, M., Takagi, S., Hieshima, Nomiyuki, H., and Yashie, O. (1997) J. Biol Chem. 272, 14893–14898.)

a new receptor for ELC/exodus3 (CCR7, Yoshida, R., Imai, T., Hieshima, K., Kusuda, J., Baba, M., Kitaura, M., Nishimura, M., Kakizaki, M., Nomiyama, H., and Yoshie, O. (1997) J. Biol. Chem. 272, 13803–13809.)

a new receptor for I-309 (CCR8, Samson, M., Stordeur, P., Labbe, O., Soularue, P., Vassart, G., and Parmentier, M. (1997) Eur. J. Immunol. 26, 3021–3028; Tiffany, H L, Lautens, L L, Gao,J-L, Pease, J., Locati, M., Combadiere, C., Modi, W., Bonner, T. I. and Murphy, P. M. (1997) J Exp. Med. 186, 165–170; Stuber-Roos, R., Loetscher, M., Legner, D. F., Clark-Lewis, I., Baggiolini, M. and Moser, B. (1997) J. Biol. Che. 272, 17251–17254)

Recently the receptor for the newly described CX3C chemokine fractalkine/neurotacin has also been identified (Imai, T., Hieshima, K., Haskell, C., Baba, M., Nagira, M., Nishimura, M., Kakizaki, M., Takagi, S., Nomiyama, H., Schall, T. J., Yoshie, O. (1997) Cell 91, 521–530.).

Chemokine receptors belong to the group of 7 transmembrane (7TM) spanning receptors and their signal transduction pathway involves pertussis toxin-sensitive G-protein and a rise in $[Ca^{2+}]_i$. Although details about the molecular events are still incomplete, a complex array of intracellular signals ultimately lead to leucocyte activation and chemotaxis (Premack, B. A. and Schall, T. J. (1996) Nature medicine 2, 1174–1178).

Chemokine receptors, like chemokines, are divided into at least three sub-families, the CXC chemokine receptors (CXCR), the CC chemokine receptors (CCR) and the CX3CR, based on their selectivity for either CXC, CC, CX3C chemokines. Ligand cross-selectively, that is CXCRs that bind CC chemokines or vice versa, is not observed. Chemokine receptors consist of 350–368 amino acids and the sequence identity amongst members of the receptor sub-families is wide (36–77%). Most chemokine receptors recognise more than one chemokine and many chemokines, including IL-8, RANTES, MIP-1α and the MCPs, bind to more than one receptor (Roos et al, J Biol Chem, 1997, 272 (28), 17521).

Current research suggests a pathophysiological role for chemokines in wide range of inflammatory states and infectious diseases. These disease states include, but are not limited to various viral, bacterial and parasital infection, rheumatoid arthritis, atherosclerosis and restenosis, psoriasis, asthma, chronic contact dermatitis, inflammatory bowel disease, multiple sclerosis, stroke, sarcoidosis, idiopathic pulmonory fibrosis as well as organ transplant rejection. Chemokines and their receptors have been recognised as targets for therapeutic agents.

The orphan 7TM receptor, HBMBU14, has been identified using EST (Expressed Sequence Tag) sequencing technology (Adams, M. D., et al. *Science* (1991) 252:1651–1656; Adams, M. D. et al., *Nature,* (1992) 355:632–634; Adams, M. D., et al., *Nature* (1995) 377 Supp:3–174) and the full-sequence length cDNA isolated (EP application no. 97307428.9; SmithKline Beecham Corp.). The sequence alignment of HBMBU 14 shows 100% identity with the published 7TM receptors TYMSTR (T-lymphocyte expressed seven transmembrane domain receptor) (Loetscher, M., et al, 1997 Current Biology 17, vol 9, 652–660), STRL-33, (Liao, F., et al, 1997, J. Exp. Med, 185, no.11, 2015–2023), and BONZO (Deng, H., et al, 1997, Nature, 388, 296–300).

TYMSTR is reported to be expressed in activated T-lymphocytes but not in freshly isolated lymphocytes and leucocytes. It has been identified as a co-receptor for human immunodeficiency virus-1 (HIV-1). Similarly, STRL33, has been reported to act as a co-receptor for both M-tropic and T-tropic HIV-1 (Liao, F., et al 1997, J. Exp Med 185, 11, 2015–23), and also as a co-receptor for SIV (Nature 1997 388, 238). STRL33 has also been found to be a co-receptor for SIV as well as HIV-1 (Deng et al, Nature 1997, 388, 296–300). BONZO mRNA has been detected in monocytes (Farzan, M., et al, 1997, J.Exp. Med 186, no3, 405–411). It has also been reported that human peripheral blood mononuclear cells express an SIV co-receptor(s) that is distinct from CCR5 (Nature 238, 388). No ligands have, to date, been identified for TYMSTR, STRL33 or BONZO.

The CXC protein, PF-4 (platelet factor -4), is a 70 residue polypeptide released from α-granules when platelets are activated by contact with collagen or other thrombotic stimuli. The most characterised activity of PF-4 is inhibition of the anticoagulant activity of heparin through blockade of its interaction with anti thrombin III and other coagulation factors, thereby promoting thrombosis at sites of platelet activation (Ruckinski B et al, 1979, Blood, 53, 47–62). PF-4 also exhibits several inflammatory activities. It is chemoattractant for monocytes and neutrophils at concentrations found in human serum (Deuel, T et al, 1981 Proc Natl Acad Sci 78, 7, 4584–87) and fibroblasts (Senior, R. M., et al, 1988 J.Cell Biol 96, 382–385). This suggests a link between initiation of thrombosis and induction of inflammation, whilst the fibroblast recruitment would enable wound healing. The carboxy terminal tridecapeptide of PF-4 has been demonstrated to be a potent chemotactic agent for monocytes (Osterman D. et al, Biochem Biophys Res Commun 1982, 107,1, 130–135). Goldman D. W. et al (1985, Immunology 54,163–172), have similarly reported the chemoattractant activity of PF-4 and a substituent dodecapeptiode, designated 59–70, towards monocytes and neutrophils. Human PF-4 has also been reported to reverse or block experimentally induced immunosuppression in mice (Barone, A. D., et al, 1988, J.Biol.Chem 263, 8710–8715; Yin, J-Z., et al, 1988 Cell Immunol 115, 221–227). PF-4 has been shown to inhibit angiogenesis by prevention of endothelial cell proliferation in response to growth factors (Maione, T. E., et al, 1990 Science 247, 77–79). Van Damme et al, 1989, Eur J Immunol 12, 2367–73 describe an additional monocyte chemotactic protein released from unfractionated cultured cells, and which they identify as PF-4. PF-4 has been shown to induce an acute local inflammatory response when dosed intradermally in the mouse (Sharpe, R. J. et al 1991, Cell Immunol, 137, 1, 72–80). The inflammatory infiltrates consisted of neutrophils and mononuclear cells. Engstad C. S. et al, (1995 J. Leukoc. Biol. 56, 5, 575–81) and Osterud, B. (1995 Blood Coag Fibrinolysis 6 Suppl 1 520–25), suggest the involvement of PF-4 in enhanced LPS-stimulated monocyte tissue factor activity. Specific binding has been demonstrated for several PF-4 related peptides eg βTG, GRO, IL-8, but the identities of cell surface receptors are not known.

We have now demonstrated that PF-4 is a ligand for the identical receptors HBMBU14, TYMSTR (T-lymphocyte expressed seven transmembrane domain receptor), STRL-33, and BONZO. This receptor will be called hereinafter the PF-4 receptor. This identification of PF-4 as a ligand for the PF-4 receptor therefore facilitates the development of screening methods for identifying agonists and antagonists of the receptor.

In a first aspect, the present invention provides for a screening method for identifying antagonists of the PF-4 receptor which method comprises using the PF-4 receptor, suitably expressed on the surface of a host cell or in a membrane preparation, or as an isolated protein, in combination with the mature form of PF-4.

The PF-4 precursor has the nucleotide sequence given in SEQ ID NO:1 and the amino acid sequence given in SEQ ID NO:2. The amino acid sequence of mature PF-4 is given in SEQ ID NO:3.

PF-4 receptor has the nucleotide sequence given in SEQ ID NO:4 and the amino acid sequence given in SEQ ID NO:5.

The invention provides for a screening method involving the use of cells which naturally express the PF-4 receptor on their surface, for example human monocytes. Another aspect of the invention concerns the use of recombinantly expressed PF-4 receptor in, for example, mammalian cells (eg. CHO and RBL cells), yeast, insect cells including Drosophila spp. and bacterial cells (eg. *E. coli*). Transfection of cells with PF-4 receptor cDNA can be achieved using standard methods, as described in, for example, Sambrook et al, Molecular Cloning, A Laboratory Manual, 2nd Ed., Cold Spring Harbor Laboratory Press, New York (1989). Receptor expression may be transient or stable. Preferably, the expression is stable. More preferably a mammalian cell line is transfected with an expression vector comprising a nucleic acid sequence encoding the PF-4 receptor, and the cell line then cultured in a culture medium, such that the receptor is stably expressed on the surface of the cell.

The invention further provides for a screening technique which involves the use of cells which express the PF-4 receptor, for example human monocytes or transfected CHO or RBL cells, in a system which measures stimulation of a chemotactic response. The cells are incubated with an effective amount of a compound added to the culture medium used to propogate the transfected cells expressing the receptor. An effective amount is a concentration sufficient to block the binding of PF-4 to the receptor, or alternatively to facilitate an agonistic effect. Inhibition of a chemotactic response to PF-4 would indicate that the particular compound is a potential antagonist of the receptor ie. the compound inhibits activation of the receptor. Incubation of the compound with the cells resulting in a chemotactic response would suggest that the compound is an agonist i.e. activates the receptor to stimulate chemotaxis.

In another aspect of the invention a screening technique involves the use of a microphysiometer which measures extracellular pH changes reflecting intracellular pH changes upon receptor activation, as described in Science, (1989) 246, 181–296. on cells which express the PF-4 receptor. Incubation of the cells expressing the PF-4 receptor with potential agonist or antagonist compounds enable a second messenger response e.g. signal transduction or pH changes to be detected. In another aspect the invention makes use of a reporter gene system, for example using the luciferase gene. In this aspect receptor activation is linked to a detectable response, for example the emission of light in the luciferase system, which can be measured to determine the effectiveness of the potential agonist or antagonist.

In another aspect of the invention, mRNA encoding the PF-4 receptor is introduced into Xenopus oocytes or melanophores thereby facilitating transient expression of the receptor. The oocytes or melanophores when incubated with the compound to be screened together with PF-4 can be monitored for antagonist effects by an inhibition of a calcium or cAMP signal, or in the case of an agonist, by detection of stimulation of a calcium or cAMP signal.

A further aspect of the invention is a screening procedure whereby the PF-4 receptor is expressed on the surface of, for example, endothelial cells, smooth muscle cells or embryonic kidney cells, in which the receptor is linked to a phospholipase C or D. Screening for an agonist or antagonist involves the detection of activation of the receptor, or inhibition of activation of the receptor, from the phospholipase second signal.

Another screening technique of the invention involves the incubation of the compound with the cells expressing the PF-4 receptor (monocytes or transfected CHO or RBL cells) with subsequent detection of an induced calcium signal or the detection of an inhibition of a PF-4-stimulated calcium signal. This method provides a means for determining the compound's potential agonist or antagonist effect.

A further screening method of the invention involves screening for PF-4 receptor inhibition by determining the inhibition of binding of labelled PF-4 to whole cells (monocytes or transfected CHO or RBL cells) or to cell membranes which have the PF-4 receptor on their surface. This assay involves incubation of the cells with compounds in the presence of a labelled form of PF-4 e.g. radiolabelled with $^{125}$Iodine. The amount of labelled ligand bound to the receptors is measured. If the compound is an antagonist the binding of labelled ligand to the receptor is inhibited.

The invention also provides for another method for screening for PF-4 inhibitors by measuring the effects on cAMP. When the PF-4 receptor is coupled to a stimulatory Gs protein PF-4 will increase cAMP levels. Eukaryotic cells expressing the PF-4 receptor, preferably transfected CHO or RBL cells, are exposed to compounds in the presence of PF-4, and reduction of cAMP accumulation is measured. In an alternative screen PF-4 signalling via its receptor is coupled to an inhibitory Gi protein. After, for example, a forskolin induced increase of cAMP, incubation with PF4 will lead to a PF4 receptor coupled reduction of cAMP levels. PF4 antagonists can be detected by measuring the prevention of this cAMP reduction.

Alternatively, an immunoassay may be used to detect PF-4 binding to its receptor by detecting the immunological reactivity of PF-4 with anti-PF-4 antibodies in the presence or absence of the test compound. The immunoassay may for example involve an antibody sandwich or an enzyme linked immunoassay (ELISA). Such methods are well known in the art and described in, for instance, Methods in Enzymology (1987, vol 154 and 155, Wu and Grossman, and Wu) and Methods in Cell and Molecular Biology (Academic Press, London).

This invention also provides a method for identifying other ligands for the PF-4 receptor, by using, for example, a standard radioligand competition assay whereby either PF-4 or the test ligand is labelled. A resulting competition assay with non-radiolabelled PF-4 or test ligand would provide a receptor affinity constant.

The systems described for identifying agonists and/or antagonists may also be used to determine ligands which bind to the receptor.

Agonists and/or antagonists may be identified from a variety of sources, for instance, from cells, cell-free preparations, chemical libraries and natural product mixtures. Such agonists and/or antagonists may be natural or modified substrates, ligands, receptors, enzymes, etc., as the case may be, of PF-4; or may be structural or functional mimetics of the polypeptide of the present invention. See Coligan et al., *Current Protocols in Immunology* 1(2):Chapter 5 (1991). Potential PF-4 receptor antagonists may include an antibody, or an oligonucleotide, which binds to the G-protein coupled receptor, but does not induce a second messenger response, such that the activity of the G-protein coupled receptor is prevented. Other potential antagonists include small molecules, e.g. small peptides or peptide-like molecules or organic molecules, which bind to the PF-4 receptor, making it inaccessible to ligands, such that normal biological activity is prevented. Potential antagonists may also include proteins that are closely related to the ligand of the PF-4 receptor, i.e. a fragment of the ligand, which have lost biological function, and which, when binding to the PF-4 receptor, elicit no response.

Another potential antagonist is a soluble form of the PF-4 receptor, for example a fragment of the receptor, which binds to PF-4 and prevents PF-4 from interacting with the membrane bound PF-4 receptor.

Compounds identified using the screen will be of use in therapy. Accordingly, in a further aspect, the present invention provides a compound identified as an agonist or an antagonist of the PF-4 receptor for use in therapy.

Agonists for PF-4 receptors may be used for therapeutic purposes, such as treatment for HIV, AIDS, rheumatoid arthritis, asthma, psoriasis, atherosclerosis and other inflammatory diseases.

Antagonists for PF-4 receptors may be used for therapeutic purposes, including but not limited to treatment for HIV, AIDS, rheumatoid arthritis, asthma, psoriasis, atherosclerosis and other inflammatory diseases.

Accordingly, in a further aspect, this invention provides a method of treating an abnormal condition related to an excess of PF-4 receptor activity and/or a ligand thereof, for example PF-4, which comprises administering to a patient in need thereof an antagonist as hereinbefore described in an amount effective to block binding of ligands to the receptor, or by inhibiting a second signal, and thereby alleviating the abnormal conditions.

This invention also provides a method of treating an abnormal condition related to an under-expression of PF-4 receptor activity and/or a ligand thereof which comprises administering to a patient in need thereof a therapeutically effective amount of an agonist compound which activates the receptor as hereinbefore described and thereby alleviate the abnormal conditions.

Identification of a ligand for the PF-4 receptor, such as PF-4, allows for the effective identification of polyclonal or monoclonal antibodies raised against the PF-4 receptor which are neutralising antibodies. Such neutralising antibodies are of use in therapy, in comparison to non-neutralising antibodies which are ineffective. Accordingly, in a further aspect, the present invention provides for the use of neutralising antibodies raised against the PF-4 receptor in therapy.

Such antibodies may be, for example, polyclonal or monoclonal antibodies. The present invention also includes chimeric, single chain or humanised antibodies, as well as Fab fragments, or the product of an Fab express on library. Various procedures well known in the art may be used for the production of such antibodies.

Antibodies generated against the PF-4 receptor may be obtained by direct injection of the isolated receptor into an animal or by administering the receptor to an animal, preferably a non-human. The antibody so obtained will then bind the receptor. For preparation of monoclonal antibodies, any technique which provides antibodies produced by continuous cell line cultures may be used, for instance the hybridoma technique (Kohler and Milstein, 1975, Nature, 256:495–497), the trioma technique, the humanB-cell hybridoma technique (Kozbor et al, 1985, Immunology Today, 4:72) and the EBV-hybridoma technique to produce human monoclonal antibodies (Cole et al, in Monoclonal Antibodies and Cancer Therapy, Alan R Liss Inc, 1975: 77–96). Techniques described for the production of single chain antibodies in U.S. Pat. No. 4,946,778 can be adapted to produce single chain antibodies to immunogenic polypeptides. In addition, transgenic mice may be used to express humanised antibodies to immunogenic polypeptides.

Compounds, including antibodies, for use in such methods of treatment will normally be provided in pharmaceutical compositions. Accordingly, in a further aspect, the present invention provides for a pharmaceutical composition comprising a compound identified as an inhibitor or an activator of the PF-4 receptor and a pharmaceutically acceptable excipient or carrier. The PF-4 agonists or antagonists may be administered in combination with a suitable pharmaceutical carrier e.g. saline, buffered saline, dextrose, water, glycerol, ethanol, or combinations of these agents. The formulation consists of a therapeutically effective amount of the agonist or antagonist, and the pharmaceutically acceptable carrier. The formulations may be administered by topical, intravenous, intraperitoneal, intramuscular, intranasal or intradermal routes, in amounts which are effective for treating and/or prophylaxis of the specific indication. In general, the formulations will be administered in an amount of at least 10 µg/kg body weight, and not in excess of about 8 mg/kg body weight. In most cases, the dosage is from about 10 µg/kg to about 1 mg/kg body weight daily, depending on the route of administration, symptoms etc.

Compounds which are active when given orally can be formulated as liquids, for example syrups, suspensions or emulsions, tablets, capsules and, lozenges.

A liquid formulation will generally consist of a suspension or solution of the compound or pharmaceutically acceptable salt in a suitable liquid carrier(s) for example, ethanol, glycerine, non-aqueous solvent, for example polyethylene glycol, oils, or water with a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

A typical suppository formulation comprises an active compound or a pharmaceutically acceptable salt thereof which is active when administered in this way, with a binding and/or lubricating agent such as polymeric glycols, gelatins or cocoa butter or other low melting vegetable or synthetic waxes or fats.

Preferably the composition is in unit dose form such as a tablet or capsule.

Each dosage unit for oral administration contains preferably from 1 to 250 mg (and for parenteral administration contains preferably from 0.1 to 25 mg) of an inhibitor of the invention.

The daily dosage regimen for an adult patient may be, for example, an oral dose of between 1 mg and 500 mg, preferably between 1 mg and 250 mg, or an intravenous, subcutaneous, or intramuscular dose of between 0.1 mg and 100 mg, preferably between 0.1 mg and 25 mg, of the active compound, or a pharmaceutically acceptable salt thereof, calculated as the free base, the compound being administered 1 to 4 times per day. Suitably the compounds will be administered for a period of continuous therapy.

Identification of a ligand for the PF-4 receptor provides a means of developing a diagnostic assay for measuring levels of PF-4 receptor in a patient. Accordingly, in a further aspect, the present invention provides for a diagnostic assay for detecting diseases or susceptibility to diseases related to abnormal activity of the PF-4 receptor. Assays used to detect levels of PF-4 in a sample derived from a patient are well known in the art and include radioimmnuoassays, Western blot analysis and ELISA assays. The invention also provides a diagnostic kit comprising PF-4.

The invention is further described in the following examples which are intended to illustrate the invention without limiting its scope. In order to facilitate understanding of the following examples certain methods and/or terms will be described. "5' and 3' untranslated sequences" refer to those sequences in mRNA flanking the protein coding region and which themselves do not code for protein. In eukaryotic mRNA the 5' and 3' untranslated region are of variable length, the 3' untranslated sequences frequently reaching several kilobases in length. It is usual to refer to these terms in the context of the corresponding DNA sequences for convenience.

"Kozak" sequence refers to a consensus nucleotide sequence surrounding the AUG start codon of a protein encoding mRNA, usually in eukaryotic organisms (see for example Kozak, M., *Nucleic Acids Res* (1984) May 11;12 (9): 3873–3893). In the present invention this sequence may be natural, ie. identified from a naturally occurring mRNA source, or synthetic, the latter being designed either by experimentation or in accordance with 'rules' known in the art. It is usual to refer to this term in the context of the corresponding DNA sequences for convenience.

All publications, including but not limited to patents and patent applications, cited in this specification are herein incorporated by reference as if each individual publication were specifically and individually indicated to be incorporated by reference herein as though fully set forth.

EXAMPLES

1. Cloning of Recombinant Human PF-4 Receptor

An EST (Expressed Sequence Tag), HBMBU14, with 37% homology to CC-CKR-2B receptor (Charo, I. F., Myers, S. J., Herman, A., Franci, C., Connolly, A. J. and Coughlin, S. R. (1994) *Proc. Natl. Acad. Sci. USA* 91, 2752–2756) was identified from the HGS (Human Genome Sciences) database. The corresponding cDNA clone was isolated and the entire cDNA insert sequenced. Sequence analysis showed that this fragment contained only a portion of the 3' coding region. In order to obtain the full-length sequence, the HBMBU14 cDNA partial fragment was amplified by PCR using the primers:
1) 5' CTA CAC CAT CCA TGG TGA CAG (SEG ID NO:6)
2) 5' TCA AGC ATT CCA TGG ACC AC (SEQ ID NO:7)
and the product was radiolabelled and used to screen the human PAC genomic library using hybridization techniques well known in the art (see for example Sambrook et al., MOLECULAR CLONING, A LABORATORY MANUAL, 2nd Ed.; Cold Spring Harbor Laboratory Press, Cold Spring Harbor, N.Y., 1989). A positive clone was identified and sequenced. Sequence analysis showed that in the corresponding region the genomic sequence is identical to the EST sequence. Primers corresponding to the 3' coding region of the HBMBU14 were designed and used to sequence the upstream coding region of the clone. The full length cDNA clone encodes 342 amino acids and which has about 38.5% identity in 342 amino acid residues with the CC-CKR-2B receptor and 34% identity in 295 amino acid residues with the human MCP-1 receptor (GENBANK Accession No. U03905).

The cDNA clone was subcloned into the mammalian expression vector pCDN (Aiyar, N., Baker, E., Wu, H.-L., Nambi, P., Edwards, R. M., Trill, J. T., Ellis, C. and Bergsma, D. J. *Mol. Cell Biochem.* 131:75–86, 1994) by PCR using PAC genomic DNA as the template and with the following primers:

```
1)5'Primer  5'  TC AGA AGCTTCACCATGGCA GAG CAT GAT TA        (SEQ ID NO:8)
                   HindIII    Translation start 2)3'Primer  5'TCT CGG ATC CCT GGC AAG GCC TAT AAC TGG AAC ATG CTG  (SEQ ID NO:9)
                  BamHI                 Translation stop
```

The primers were designed to remove all 5' and 3' untranslated regions (UTRs) and to introduce useful restriction sites to aid subsequent subcloning of this PCR fragment into the pCDN vector; HindIII and BanHI flanking the coding region to the 5' and 3' respectively. Primer (1) also introduced a consensus Kozak sequence (underlined) in order to maximise expression from this plasmid construct. The sequences of the HBMBU14 coding region and the flanking PCR primers in the resultant expression construct were confirmed.

2. Stable Expression of PF-4 Receptor in Mammalian Cell Lines

The pCDN vector carries both G418 resistance and dihydrofolate reductase genes for selection and amplification.

Stable cell lines of PF-4 receptor in CHO and RBL-2H3 cells were obtained by electroporation of the pCDN:PF-4 receptor vector followed by clonal selection using G418 at 400 ug/ml in the growth medium. After 3 weeks in the selection medium individual clones were picked and expanded for further analysis.

A HEK293 stable cell line of PF-4 receptor was obtained by calcium phosphate precipitation followed by clonal selection using G418 at 400 ug/ml as described above.

The CHO, RBL-2H3 and HEK293 lines were screened for high level receptor expression by Northern blot analysis using RNA isolated from the G418 lines and as hybridization probe the coding sequence of PF-4 receptor. From this screen, the clonal cell lines producting the highest PF-4 receptor RNA levels were chosen for further study.

3. Monocyte Isolation

Human peripheral blood monocytes are prepared from the blood of normal healthy volunteers, essentially as described by Boyum (*Methods in Enzymology* (Academic Press, New York and London) 108, 88–102). Blood is collected into anticoagulant (one part 50 mM EDTA, pH 7.4, to nine parts blood), then centrifuged for 5 minutes at 600 g. The upper layer of platelet-rich plasma is removed and centrifuged for 15 minutes at 900 g, to pellet the platelets. The upper layer of platelet-poor plasma is removed and added back to the packed red cells; the pelleted platelets are discarded. Dextran T500 is added (10 volumes EDTA blood to one volume 6% (w/v) dextran in 0.9% (w/v) NaCl) and the erythrocytes are allowed to sediment at unit gravity for 30 minutes. The resultant leukocyte-rich plasma is removed and centrifuged for 5 minutes at 400 g. The cell pellet is resuspended in 5 ml of the supernatant, and the suspension is underlayered with 3 ml NycoPrep, then centrifuged for 15 minutes at 600 g. The mononuclear layer at the interface between the plasma and the NycoPrep isremoved and washed through PBS by centrifugation for 5 minutes at 400 g. The mononuclear layer typically contained $\geq 80\%$ monocytes, determined by staining cytocentrifuge preparations for non-specific esterase using $\alpha$-naphthyl-butyrate. Cell viability (typically >95%) is assessed as the ability to exclude trypan blue.

Figure 1:
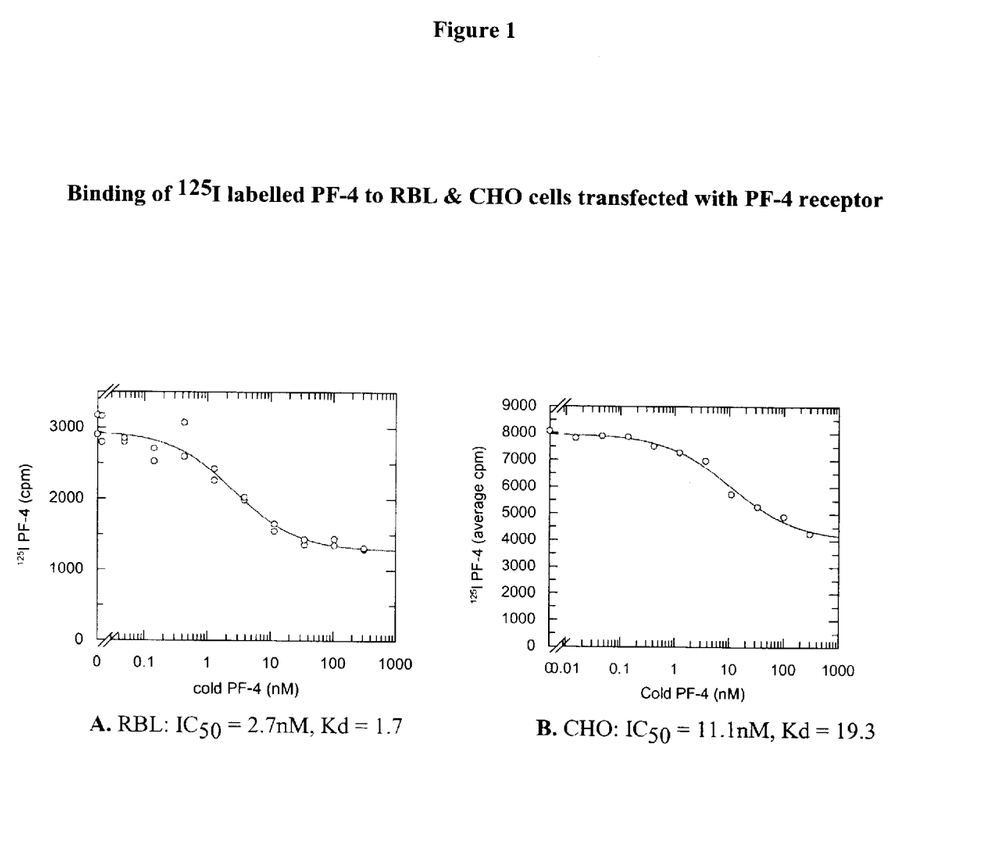

4. Ligand Binding Studies With Receptor
a. Whole Cell Assay $^{125}$I-labelled PF-4 was incubated with 1–2×10$^6$ cells (monocytes or transfected RBL or transfected CHO) in the presence or absence of increasing concentrations of unlabelled PF-4 for 15 minutes at 37° C. in a 96 well plate. Following incubation, the cells were washed and collected onto a polyethylenimine-treated Whatman GF/C filter, using a Brandell cell harvester. Filters were washed and radioactivity bound to the filters was counted in a $\gamma$-counter. FIG. 1A shows the binding results of RBL cells transfected with the PF-4 receptor and FIG. 1B the results with PF-4 receptor transfected CHO cells.

b. Cell Membrane Assay (Using Membranes From Transfected RBL or CHO Cells)

$^{125}$I-labelled PF-4 was incubated with 50 $\mu$g of membrane suspension in the presence or absence of increasing concentrations of unlabelled PF-4 for 2 hours at room temperature in a 96-well plate. Following incubation, the membranes were washed and collected onto a polyethylenimine-treated Whatman GF/C filter, using a Packard harvester. The plate was oven dried and radioactivity bound to the filter plate was counted in a $\gamma$-counter.

5. Functional Studies With Receptor
a. Chemotaxis

Figure 2:
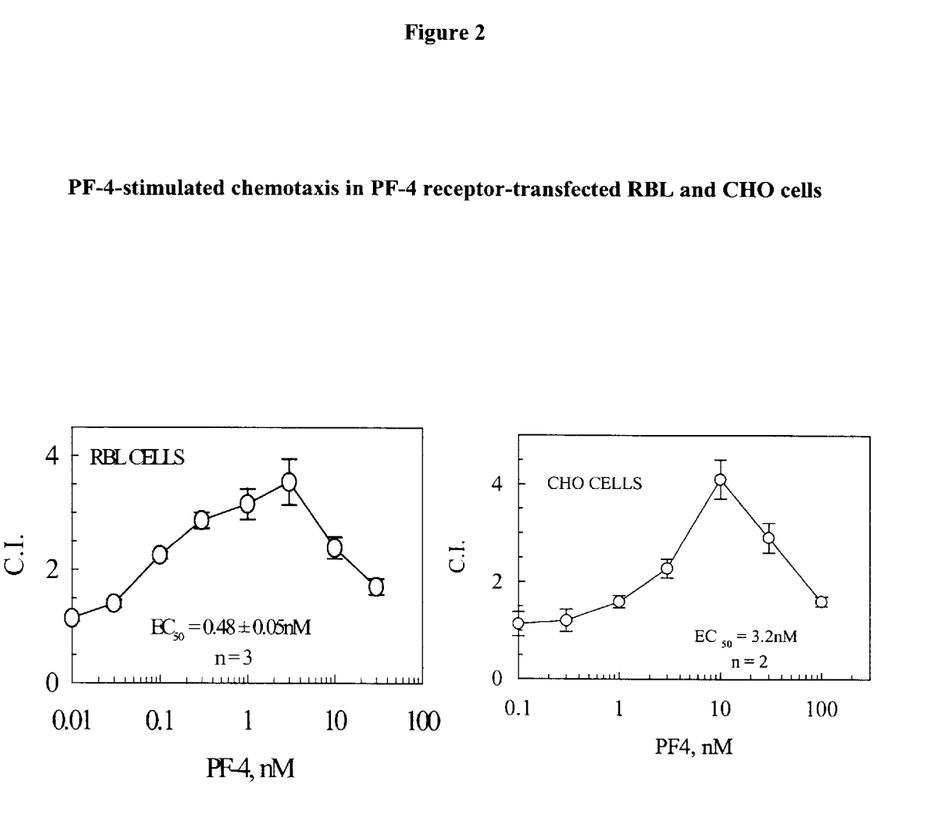

The chemoattractant activity of PF-4 towards RBL or CHO cells transfected with PF-4 receptor was monitored using a 96-well chemotaxis assay (see FIG. 2). RBL or CHO cells transfected with an unrelated orphan chemokine receptor were used as controls and did not respond to PF-4. Briefly, cells which have migrated across a polycarbonate filter with pore size 5 μm (RBL cells) or 8 μm (CHO cells) towards the PF-4 (0–30 nM), following incubation at 37° C. and 5% $CO_2$ humidified air, were quantified calorimetrically from a standard curve relating cell density to absorbance at 590 nm. The colorimetric end point derives from cellular reduction of 3-[4,5,dimethylthiazol-2-yl]-2,5, diphenyltetrazolium bromide from its formazan product.

Figure 3:
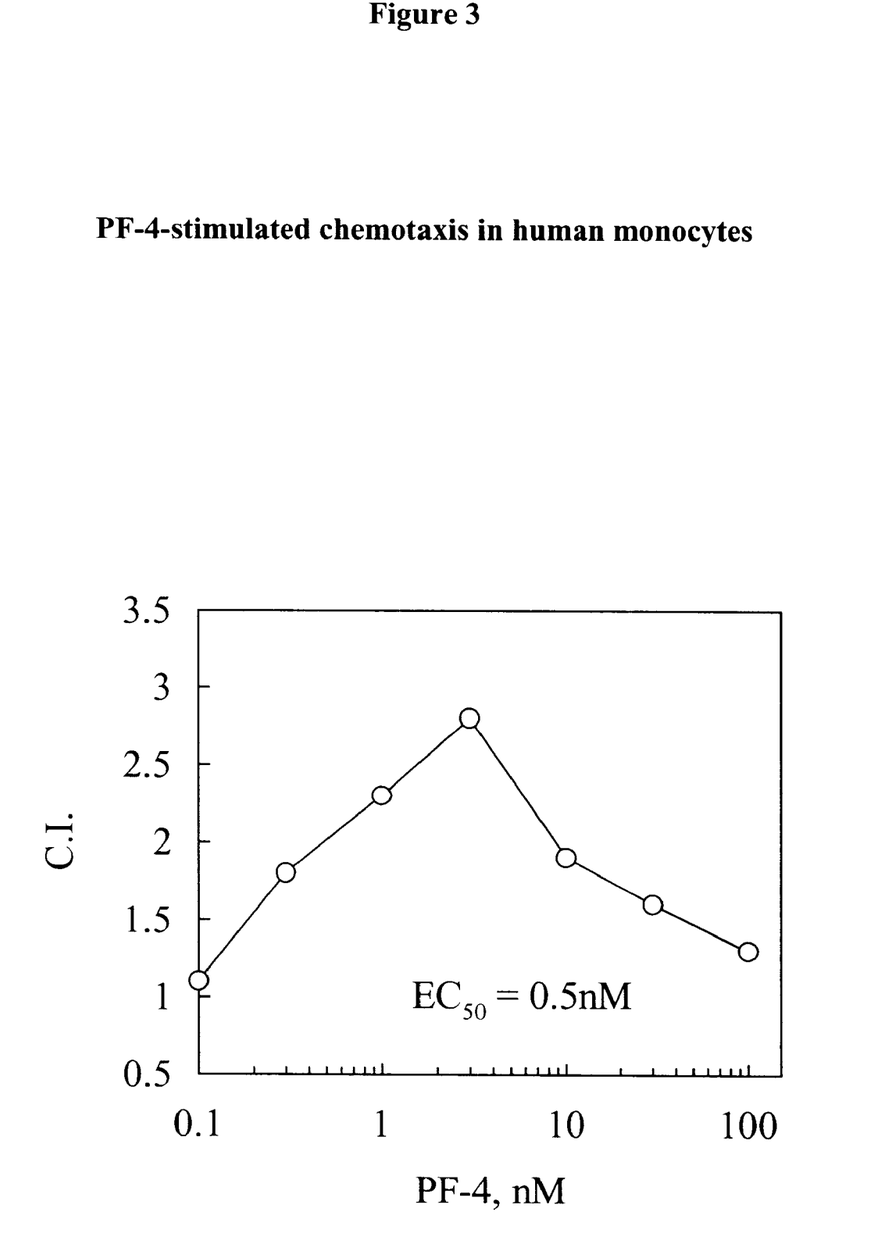

The chemoattractant activity of PF-4 towards freshly isolated human monocytes was determined using a 48-well modified Boyden microchemotaxis chamber. Numbers of cells migrating across a polycarbonate filter (5 μm pore size) following incubation at 37° C. and 5% $CO_2$ humidified air were quantified by light microscopy of Diff-Quik stained filters, using a ×40 objective and ×10 ocular containing a 10 $mm^2$ counting grid (FIG. 3).

b. Calcium Mobilisation

The ability of PF-4 or other chemokines to elicit a calcium signal in monocytes or cells transfected with the PF-4 receptor to elicit a calcium signal can be monitored by measuring the increased fluorescence of fura-2 or fluo-3.

6. mRNA Expression in Different Cell Types

PolyA RNA was isolated from various cell types using guanidinum thiocyanate acid-phenol method. Poly A RNA is isolated using oligo dT column. RNA dot blot analysis is performed with a template manifold apparatus (Schleicher & Schuell, Keene, N.H.) to assure uniform dot size. Poly A RNA is applied using 0.5 ug of RNA. The RNA samples are denatured by adjusting them to 1M formaldehyde and heating them to 55° C. for 15 min. The samples are diluted into 20 volumes of 3 M NaCl containing 0.3 M trisodium citrate and applied to nitrocellulose filters under a gentle vacuum. The filters are washed with additional diluted, baked at 80° C. for 2 h and then hybridized under high strengency in 50% formamide, 5×SSPE, 5×Denhardt's reagent, 0.1% SDS, and 100 ug/ml yeast tRNA. The blots are washed with 0.1×SSC, 0.1% SDS at 50° C. and exposed to X-ray film for 48 h at −70° C. Quantitation of the dots is performed using Phospho-Imaging analysis.

Poly A RNA was isolated from monocytes, macrophages, foam cells, MonoMac, Thp1, PBL, EOL3, neutrophils, T-cells, SM cells and endothelial cells. Relatively high level of expression was observed in monocytes, monomac, THP1, and PBL cells. Low level of expression was observed in FOL3 and endothelial cells.

7. Membrane Preparation and High Throughput Screen for the PF-4 Receptor

For the discovery of antagonists and agonists of the PF-4 receptor, a PF-4 binding competition assay is most useful. As a source of the PF-4 receptor, CHO or HEK 293 cells, stably transfected with the PF-4 receptor, could be used although other cells transfected with the PF-4 receptor or cells that naturally show a high level expression of the PF-4 receptor could also be employed. Typically the culture of cells expressing the PF-4 receptor (see example 1) is scaled up to 30 L and cells are recovered by centrifugation at 600×g for 10 min. The cell pellet is then frozen in liquid nitrogen. Pellets usually contain around $10^9$ cells. For membrane isolation, pellets are freeze/thawed 3 times. They are then resuspended in ice cold 10 mM Tris (pH 7.5), 1 mM EDTA (sodium salt) (40 mls/le8 cells) and homogenized using a Dounce (glass/glass) homogenizer (20–25 strokes), followed by a Polytron suspension with 3–10 sec pulses on a ¾ setting (Brinkman tissue homogenizer). This suspension is centrifuged at 300×g for 10 min. Pellet is discarded and the supernatent fraction is centrifuged at 40,000×g (Sorvall SS-34: 18,000 rpm) for 30 min. at 4° C. Pellet is resuspended in homogenizing buffer using the polytron and washed one time. The pellet is resuspended in assay buffer (50 mM Tris pH 7.5) at a concentration of 1–4 mg protein/ ml.

Membranes obtained this way are suitable for the set-up of a high throughput PF-4 binding competition assay to search for compounds that interfere in the ligand-receptor interaction. The total binding of PF-4 to these membranes is first tested to be linear with the amount of membranes used. The time period to reach equilibrium binding at a suitable temperature is also. established and is in our experience about 1 h at a temperature of 20° C. For the screening assay typically 25 μg of membrane protein per well is used in a total volume of 100 μl buffer containing 50 mM HEPES, 1 mM $CaCl_2$, 5 mM $MgCl_2$ and 0.5% Bovine serum albumin (western blot quality), pH 7.4. The concentration of $^{125}I$-PF-4 is typically 1–2 nM and 75,000 cpm /well. Specific binding of labeled PF-4 should be displaced completely by unlabeled PF-4 at concentrations of 100 nM or more. The compounds to be tested are typically disolved and added in DMSO and final concentrations of DMSO in the assay are 1% or less. After incubation the contents of the wells are harvested on a polyethyleneimine-treated GF/C filter using a 96 well plate cell harvester and the filters is washed four times with typically 1 ml icecold wash buffer containing 20 mM HEPES 0.5M NaCl pH 7.4. To determine any antagonists of labelled PF-4 binding, the filters are counted.

Alternatively, PF4 could be tagged with either a fluorescent label (page 415–421, Handbook of Fluorescent Probes and Research Chemicals 6th Edition, RP Haugland editor, Molecular Probes), a biotin label or a enzyme tag like the alkaline phosphatase SEAP-tag (Hishiema,K. et al, J Biol Chem. 1997, 272, 5846–53). The binding assay itself would typically be very similar to that described for radiolabeled PF4. Detection of bound PF4 would be by measuring fluorescence, binding of streptavadin or by measuring enzyme activity. As an alternative for detection of $^{125}I$-PF4 by filter binding a SPA assay (Amersham) might be used.

Active compounds are further evaluated for their effect on ligand (PF-4) induced transient increases in intracellular calcium concentration. This assay is also able to distinguish whether compounds identified by the membrane binding assay are antagonists or agonists.

For measurements of cytosolic $Ca^{2+}$ concentrations, appropriate cell lines transfected with the PF-4 receptor should be used. Appropriate cells include CHO cells and HEK 293 cells, if required co-transfected with appropriate G-coupling proteins. For the intracellular calcium concentration measurements cells are incubated with 0.5 μM FURA-2AM for 30 minutes at 37° C. in HEPES-buffered saline (145 mM NaCl, 5 mM KCl, 1 mM $MgCl_2$, 10 mM HEPES and 10 mM glucose), pH 7.4 at 37° C., supplemented with 1% albumin (w/v) and 1 mM $CaCl_2$. After loading with FURA-2 the cells are centrifuged for 5 minutes at 300 g, then resuspended in buffer containing no added albumin, to a cell density of $1.5×10^6$ cells/ml, and kept at room temperature until use. Typically, this protocol results in a cytosolic FURA-2 concentration of approx. 100 μM. Serial dilutions of chemokines in PBS+0.1% albumin (w/v)—sterile-filtered—are added to aliquots (0.7 ml) of cell suspension. FURA-2 fluorescence is measured at 37° C. in a single excitation, single emission (500 nm) wavelength Perkin Elmer LS5 fluorimeter. $[Ca^{2+}]_i$ are calculated from changes in fluorescence measured at a single excitation wavelength of 340 nm, as described by Grynkiewicz, G., Poenie, M., & Tsien, R. Y. (1985) *J. Biol. Chem.* 260, 3440–3450. Compound are normally added to the cells in DMSO solutions (final concentration less than 0.2%) and if compounds have agonist properties an effect on $[Ca^{2+}]_i$ is observed. Receptor function antagonism is evident if compounds are able depress the signal induced by the subsequent addition of PF-4 at a concentration shown to give a 75% maximal calcium signal in the absence of any compound.

The effects of compounds on PF-4 binding and response in physiologically relevant cells expressing the PF-4 receptor are normally tested in freshly isolated peripheral blood monocytes or peripheral blood lymphocytes.

What is claimed is:

1. A method for identifying agonists or antagonists to the polypeptide set forth in SEQ ID NO: 5 comprising:
    (a) contacting a candidate compound with the polypeptide set forth in SEQ ID NO: 5 in the presence of labeled or unlabeled PF-4; and
    (b) assessing the ability of said candidate compound to compete with the binding of PF-4 to the polypeptide set forth in SEQ ID NO: 5.

2. The method of claim 1 wherein said polypeptide is contacted with labeled PF-4, wherein said labeled PF-4 is labeled using a radiolabel, a biotin, enzyme or a fluorogenic label and the amount of labeled PF-4 bound by the polypeptide is measured in the presence and absence of said candidate compound.

3. The method of claim 1, wherein said method is used to identify chemokine ligands for the receptor.

4. The method of claim 1 wherein said polypeptide set forth in SEQ ID NO: 5 is on the surface of a host cell, on a cell membrane or on a solid support.

5. The method of claim 4 further comprising the step of determining whether the candidate compound affects a signal generated by the polypeptide set forth in SEQ ID NO: 5 at the surface of the cell, wherein a candidate compound which increases production of said signal is identified as an agonist.

6. The method of claim 4 further comprising the step of determining whether the candidate compound affects a signal generated by the polypeptide set forth in SEQ ID NO: 5 at the surface of the cell, wherein a candidate compound which diminishes production of said signal is identified as an antagonist.

7. The method of claim 4 wherein said candidate compound is added to the culture medium used to propagate the host cells expressing said polypeptide.

8. A method for identifying compounds which inhibit or enhance activity of a PF-4 receptor, said method comprising:
    (a) transforming a cell with an expression vector comprising a polynucleotide that encodes the polypeptide set forth in SEQ ID NO: 5 such that said cell expresses said polypeptide;
    (b) contacting a candidate compound with said polypeptide;
    (c) measuring the change in a functional response or a second messenger system associated with said receptor.

9. The method of claim 8 wherein said cell is a melanophore.

10. The method of claim 8 wherein said cell is a Xenopus oocyte.

11. The method of claim 8 wherein said receptor is linked to a phospholipase C or D.

12. The method of claim 8 further comprising the step of determining the production of cAMP of said cell.

* * * * *

SEQUENCE LISTING

<160> NUMBER OF SEQ ID NOS: 9

<210> SEQ ID NO 1
<211> LENGTH: 439
<212> TYPE: DNA
<213> ORGANISM: HOMO SAPIENS

<400> SEQUENCE: 1

```
ccgcagcatg agctccgcag ccgggttctg cgcctcacgc cccgggctgc tgttcctggg    60
gttgctgctc ctgccacttg tggtcgcctt cgccagcgct gaagctgaag aagatgggga   120
cctgcagtgc ctgtgtgtga agaccacctc ccaggtccgt cccaggcaca tcaccagcct   180
ggaggtgatc aaggccggac cccactgccc cactgcccaa ctgatagcca cgctgaagaa   240
tggaaggaaa atttgcttgg acctgcaagc cccgctgtac aagaaaataa ttaagaaact   300
tttggagagt tagctactag ctgcctacgt gtgtgcattt gctatatagc atacttcttt   360
tttccagttt caatctaact gtgaaagaaa cttctgatat ttgtgttatc cttatgattt   420
taaataaaca aataaatc                                                  439
```

<210> SEQ ID NO 2
<211> LENGTH: 101
<212> TYPE: PRT
<213> ORGANISM: HOMO SAPIENS

<400> SEQUENCE: 2

```
Met Ser Ser Ala Ala Gly Phe Cys Ala Ser Arg Pro Gly Leu Leu Phe
  1               5                  10                  15

Leu Gly Leu Leu Leu Leu Pro Leu Val Val Ala Phe Ala Ser Ala Glu
             20                  25                  30

Ala Glu Glu Asp Gly Asp Leu Gln Cys Leu Cys Val Lys Thr Thr Ser
         35                  40                  45

Gln Val Arg Pro Arg His Ile Thr Ser Leu Glu Val Ile Lys Ala Gly
     50                  55                  60

Pro His Cys Pro Thr Ala Gln Leu Ile Ala Thr Leu Lys Asn Gly Arg
 65                  70                  75                  80

Lys Ile Cys Leu Asp Leu Gln Ala Pro Leu Tyr Lys Lys Ile Ile Lys
                 85                  90                  95

Lys Leu Leu Glu Ser
            100
```

<210> SEQ ID NO 3
<211> LENGTH: 70
<212> TYPE: PRT
<213> ORGANISM: HOMO SAPIENS

<400> SEQUENCE: 3

```
Glu Ala Glu Glu Asp Gly Asp Leu Gln Cys Leu Cys Val Lys Thr Thr
  1               5                  10                  15
```

```
Ser Gln Val Arg Pro Arg His Ile Thr Ser Leu Glu Val Ile Lys Ala
            20                  25                  30

Gly Pro His Cys Pro Thr Ala Gln Leu Ile Ala Thr Leu Lys Asn Gly
        35                  40                  45

Arg Lys Ile Cys Leu Asp Leu Gln Ala Pro Leu Tyr Lys Lys Ile Ile
    50                  55                  60

Lys Lys Leu Leu Glu Ser
65                  70

<210> SEQ ID NO 4
<211> LENGTH: 1026
<212> TYPE: DNA
<213> ORGANISM: HOMO SAPIENS

<400> SEQUENCE: 4
```

| | | | | | |
|---|---|---|---|---|---|
| atggcagagc | atgattacca | tgaagactat | gggttcagca | gtttcaatga | cagcagccag | 60 |
| gaggagcatc | aagacttcct | gcagttcagc | aaggtctttc | tgccctgcat | gtacctggtg | 120 |
| gtgtttgtct | gtggtctggt | ggggaactct | ctggtgctgg | tcatatccat | cttctaccat | 180 |
| aagttgcaga | gcctgacgga | tgtgttcctg | gtgaacctac | ccctggctga | cctggtgttt | 240 |
| gtctgcactc | tgcccttctg | ggcctatgca | ggcatccatg | aatgggtgtt | tggccaggtc | 300 |
| atgtgcaaga | gcctactggg | catctacact | attaacttct | acacgtccat | gctcatcctc | 360 |
| acctgcatca | ctgtggatcg | tttcattgta | gtggttaagg | ccaccaaggc | ctacaaccag | 420 |
| caagccaaga | ggatgacctg | ggcaaggtc | accagcttgc | tcatctgggt | gatatccctg | 480 |
| ctggtttcct | tgcccaaat | tatctatggc | aatgtcttta | atctcgacaa | gctcatatgt | 540 |
| ggttaccatg | acgaggcaat | tccactgtg | gttcttgcca | cccagatgac | actggggttc | 600 |
| ttcttgccac | tgctcaccat | gattgtctgc | tattcagtca | taatcaaaac | actgcttcat | 660 |
| gctggaggct | tccagaagca | cagatctcta | aagatcatct | tcctggtgat | ggctgtgttc | 720 |
| ctgctgaccc | agatgccctt | caacctcatg | aagttcatcc | gcagcacaca | ctgggaatac | 780 |
| tatgccatga | ccagctttca | ctacaccatc | atggtgacag | aggccatcgc | atacctgagg | 840 |
| gcctgcctta | accctgtgct | ctatgccttt | gtcagcctga | gtttcgaaa | gaacttctgg | 900 |
| aaacttgtga | aggacattgg | ttgcctccct | taccttgggg | tctcacatca | atggaaatct | 960 |
| tctgaggaca | attccaagac | tttttctgcc | tcccacaatg | tggaggccac | cagcatgttc | 1020 |
| cagtta | | | | | | 1026 |

<210> SEQ ID NO 5
<211> LENGTH: 342
<212> TYPE: PRT
<213> ORGANISM: HOMO SAPIENS

<400> SEQUENCE: 5

Met Ala Glu His Asp Tyr His Glu Asp Tyr Gly Phe Ser Ser Phe Asn
1               5                   10                  15

Asp Ser Ser Gln Glu Glu His Gln Asp Phe Leu Gln Phe Ser Lys Val
            20                  25                  30

Phe Leu Pro Cys Met Tyr Leu Val Val Phe Val Cys Gly Leu Val Gly
        35                  40                  45

Asn Ser Leu Val Leu Val Ile Ser Ile Phe Tyr His Lys Leu Gln Ser
    50                  55                  60

Leu Thr Asp Val Phe Leu Val Asn Leu Pro Leu Ala Asp Leu Val Phe
65                  70                  75                  80

-continued

```
Val Cys Thr Leu Pro Phe Trp Ala Tyr Ala Gly Ile His Glu Trp Val
                 85                  90                  95
Phe Gly Gln Val Met Cys Lys Ser Leu Leu Gly Ile Tyr Thr Ile Asn
            100                 105                 110
Phe Tyr Thr Ser Met Leu Ile Leu Thr Cys Ile Thr Val Asp Arg Phe
            115                 120                 125
Ile Val Val Val Lys Ala Thr Lys Ala Tyr Asn Gln Gln Ala Lys Arg
        130                 135                 140
Met Thr Trp Gly Lys Val Thr Ser Leu Leu Ile Trp Val Ile Ser Leu
145                 150                 155                 160
Leu Val Ser Leu Pro Gln Ile Ile Tyr Gly Asn Val Phe Asn Leu Asp
                165                 170                 175
Lys Leu Ile Cys Gly Tyr His Asp Glu Ala Ile Ser Thr Val Val Leu
            180                 185                 190
Ala Thr Gln Met Thr Leu Gly Phe Phe Leu Pro Leu Leu Thr Met Ile
            195                 200                 205
Val Cys Tyr Ser Val Ile Ile Lys Thr Leu Leu His Ala Gly Gly Phe
        210                 215                 220
Gln Lys His Arg Ser Leu Lys Ile Ile Phe Leu Val Met Ala Val Phe
225                 230                 235                 240
Leu Leu Thr Gln Met Pro Phe Asn Leu Met Lys Phe Ile Arg Ser Thr
                245                 250                 255
His Trp Glu Tyr Tyr Ala Met Thr Ser Phe His Tyr Thr Ile Met Val
            260                 265                 270
Thr Glu Ala Ile Ala Tyr Leu Arg Ala Cys Leu Asn Pro Val Leu Tyr
            275                 280                 285
Ala Phe Val Ser Leu Lys Phe Arg Lys Asn Phe Trp Lys Leu Val Lys
        290                 295                 300
Asp Ile Gly Cys Leu Pro Tyr Leu Gly Val Ser His Gln Trp Lys Ser
305                 310                 315                 320
Ser Glu Asp Asn Ser Lys Thr Phe Ser Ala Ser His Asn Val Glu Ala
                325                 330                 335
Thr Ser Met Phe Gln Leu
            340

<210> SEQ ID NO 6
<211> LENGTH: 21
<212> TYPE: DNA
<213> ORGANISM: HOMO SAPIENS

<400> SEQUENCE: 6
ctacaccatc catggtgaca g                                              21

<210> SEQ ID NO 7
<211> LENGTH: 20
<212> TYPE: DNA
<213> ORGANISM: HOMO SAPIENS

<400> SEQUENCE: 7
tcaagcattc catggaccac                                                20

<210> SEQ ID NO 8
<211> LENGTH: 31
<212> TYPE: DNA
<213> ORGANISM: HOMO SAPIENS

<400> SEQUENCE: 8
```

-continued

```
tcagaagctt caccatggca gagcatgatt a                              31

<210> SEQ ID NO 9
<211> LENGTH: 39
<212> TYPE: DNA
<213> ORGANISM: HOMO SAPIENS

<400> SEQUENCE: 9
tctcggatcc ctggcaaggc ctataactgg aacatgctg                      39
```